United States Patent [19]

Dunning et al.

[11] Patent Number: 4,964,852
[45] Date of Patent: Oct. 23, 1990

[54] DOUCHE CONTAINER AND NOZZLE WITH INTERMEDIATE ONE-WAY VALVE

[75] Inventors: Walter B. Dunning, Pleasanton, Calif.; John P. Kinsley, Crystal Lake, Ill.

[73] Assignee: Tambrands, Inc., Lake Success, N.Y.

[21] Appl. No.: 415,936

[22] Filed: Oct. 5, 1989

Related U.S. Application Data

[63] Continuation-in-part of Ser. No. 256,043, Oct. 11, 1988, abandoned.

[51] Int. Cl.$^5$ .............................................. A61M 1/06
[52] U.S. Cl. .................................... 604/75; 222/212; 222/493; 222/525
[58] Field of Search ................... 604/75, 212-213, 604/316, 39, 42; 222/525, 493-494, 212

[56] References Cited

U.S. PATENT DOCUMENTS

| | | | |
|---|---|---|---|
| 3,949,934 | 4/1976 | Gioglio | 222/62.5 |
| 4,147,306 | 4/1979 | Bennett | 222/212 X |
| 4,200,097 | 4/1980 | Hobbs, Jr. et al. | 128/251 |
| 4,253,588 | 3/1981 | Lester et al. | 222/153 |
| 4,513,891 | 4/1985 | Hain et al. | 222/213 |
| 4,568,004 | 2/1986 | Gioncalues | 222/207 |

FOREIGN PATENT DOCUMENTS 0177456 4/1986 European Pat. Off. .

Primary Examiner—C. Fred Rosenbaum
Assistant Examiner—C. Maglione
Attorney, Agent, or Firm—A. Thomas S. Safford

[57] ABSTRACT

A one-way valve positioned between the nozzle and container of a disposable douche, which is opened and closed by axial movement of the nozzle relative to the container, permitting discharge of the douche contents without permitting backflow. The neck of the container opening having an intermediate cap with axial discharge holes and a flexible valve disk overlying such holes all within the bore of the base of the nozzle. In the closed position, the inner shoulder of the nozzle base seat against the flexible valve disk presenting discharge of the contents through the discharge opening of the intermediate cap. With the axial displacement of the nozzle away from the main body of the container the valve disk, freed of the internal restraining shoulders of the nozzle base, can flex to permit flow of the contents of the container into the nozzle. The nozzle base's bore and the intermediate container cap have slidable inner-fitting surfaces to prevent fluid discharge therebetween, such that all fluid is discharged out of appropriate nozzle openings in the free end of the nozzle.

31 Claims, 4 Drawing Sheets

U.S. Patent  Oct. 23, 1990  Sheet 1 of 4  4,964,852
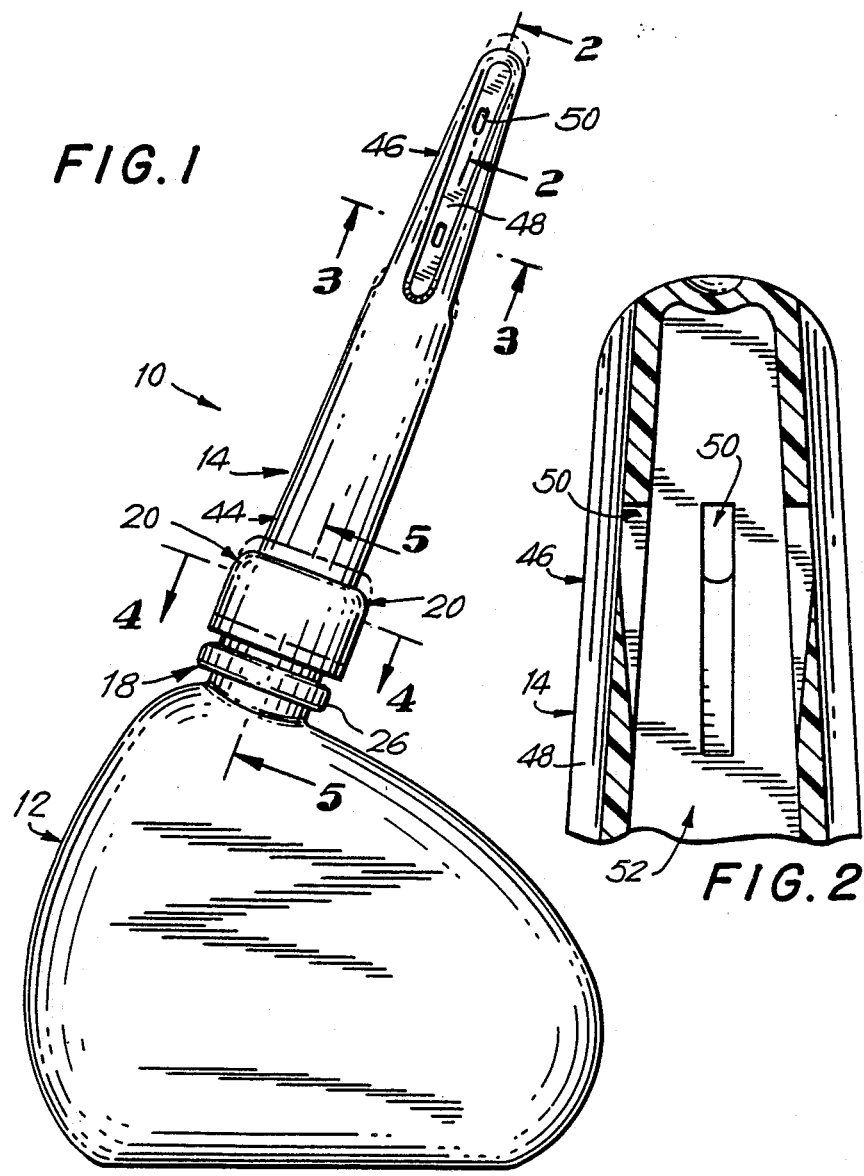
FIG.1
FIG.2
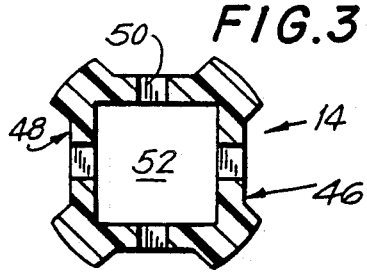
FIG.3
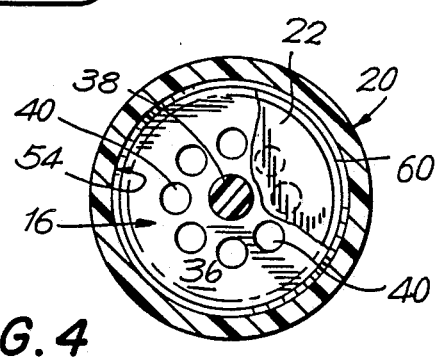
FIG.4

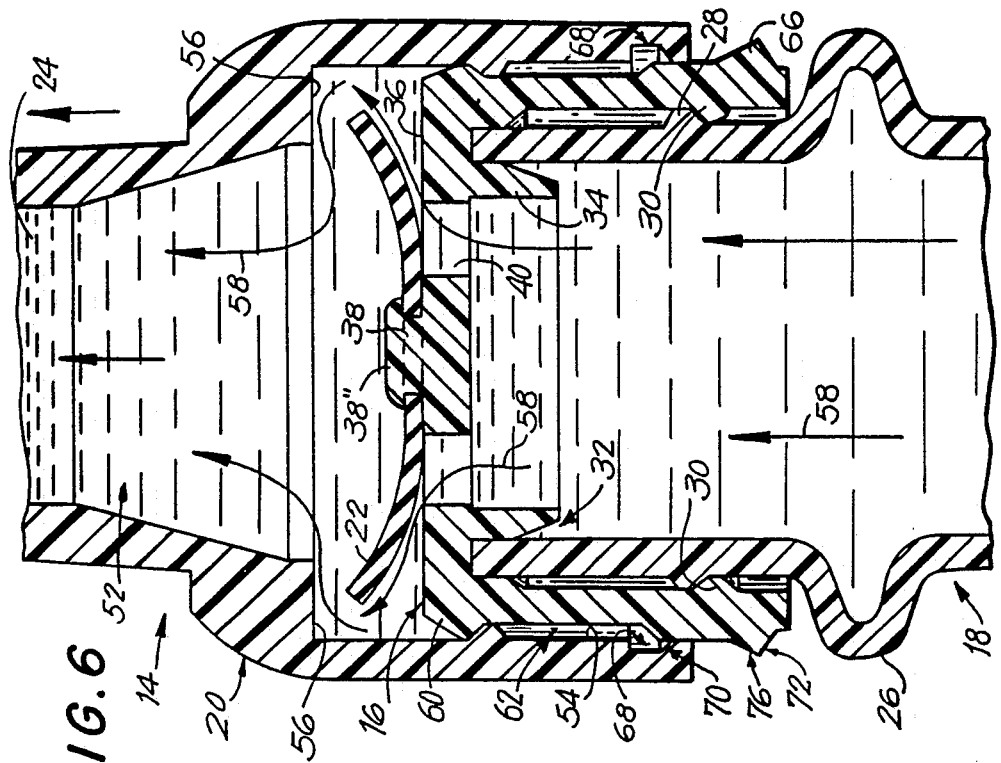
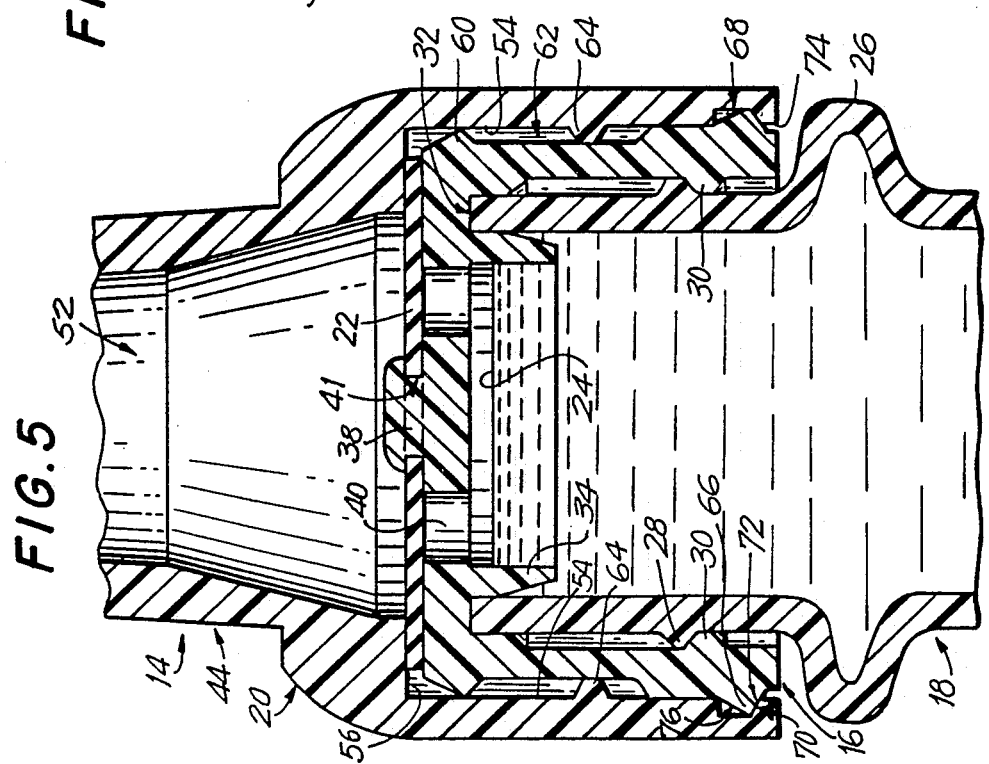

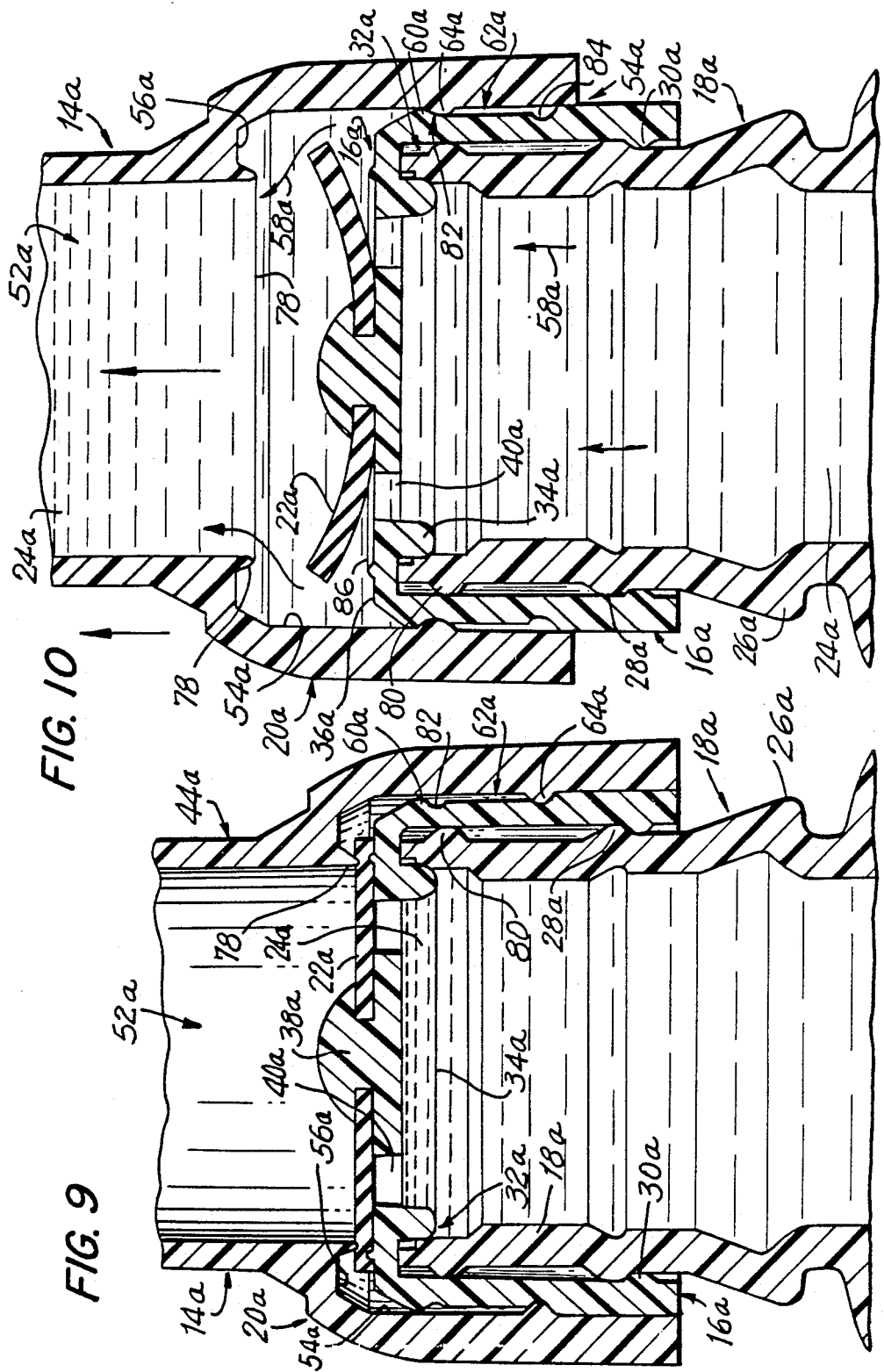

though the nozzle is still in the open position, the resilient disk naturally flattens back against the cap outlets and thus acts as a check valve to prevent liquid and/or air backflow into the container.

DOUCHE CONTAINER AND NOZZLE WITH INTERMEDIATE ONE-WAY VALVE

This is a continuation-in-part application of application Ser. No. 256,043 filed Oct. 11, 1988, now abandoned.

BACKGROUND OF THE INVENTION

1. Field of the Invention

The present invention concerns a douche container with nozzle assembly, and more particularly is directed to a disposable douche assembly having a collapsible container and an associated nozzle with an intermediate one-way valve. In the present invention, the intermediate valve functions as a check valve when in the open position and is actuated by axial movement of the nozzle relative to the container between an extended open position and a retracted closed position.

2. Related Art

Douche containers having attached nozzles with one way valves of varying complexity for preventing the return flow of fluid into the douche container are known. Some are disposable. Several of these use a very simple valve in the form of a resilient gasket positioned between the neck of the douche container and the nozzle and have a simple slit in the gasket which opens under pressure, such as by squeezing the container, and closes upon release of pressure due to the resiliency of the gasket material. See, for example, U.S. Pat. Nos. 2,869,545; 2,881,760; and 3,507,280. These obviously lack secure closure and are subject to leaking.

Other similar patents show somewhat more complex valves. For example, U.S. Pat. No. 4,200,097 teaches a disposable double valve douche container having a retractable nozzle with a slide closure valve at the bottom of the nozzle stem and one way ball check valve positioned just above the slide valve.

See also European Patent Publication 0 177 456 which discloses a somewhat similar single valve douche container also having an axially retractable nozzle. Instead of an intermediate valve between the container and the nozzle, this publication shows a slide-plug valve combination on the upper end of the nozzle having a dual groove with detent position structure. However, this is not a one-way valve.

U.S. Pat. No. 3,986,509 shows also a push-pull valve mechanism, but located between the nozzle and the container. This also is not a one-way valve.

Flexible disk valves of various types are known outside the douche art. U.S. Pat. No. 3,618,825 shows a check valve diaphragm that provides for fluid discharge through a central hole (not past the peripheral edges). U.S. Pat. No. 3,949,934 shows a food container with a screw top outlet having a flexible disk functioning as a one-way valve with peripheral discharge. See also Dutch Pat. No. 67878.

OBJECTS OF THE INVENTION

It is an object of the invention to provide a low-cost high-quality disposable douche container and valved nozzle assembly, which is easy to manufacture at high production volumes with a minimum of parts and without the need for unduly complex manufacturing machinery.

It is another object of this invention to provide for a douche container and nozzle assembly which has an easily actuated and reliable valve, that will not leak during storage and will not close during use.

It is a further object of this invention to greatly reduce, and even eliminate, the undesirable feature of many prior art douches which introduce relatively large amounts of air into the vagina by providing in the present invention a structure such that when the valve of the douche assembly is placed in the open position and the nozzle is primed with liquid from the container, the initial prime is maintained and no further priming is required even though pressure is removed from the container.

It is yet another object of this invention to provide such a douche container and nozzle assembly with a valve which is an on-off valve that additionally functions as a check valve when in the on position, such that (1) when in the closed position, it prevents liquid or air outflow or inflow from the container through the nozzle, and (2) when in the open position, it permits free liquid outflow from the container through the nozzle when pressure is applied to the container, while preventing backflow of liquid or air into the container (e.g. when pressure is removed from the container).

It is an additional object of this invention to provide for a douche container and nozzle assembly wherein all the liquid douching contents of the container can be completely expelled with no backflow or other wastage.

These and other objects are met by the present invention.

SUMMARY OF THE INVENTION

The present invention is directed, inter alia to a disposable douche container and nozzle assembly shown in the preferred form for vaginal use, advantageously for dispensing a cleansing solution; which in its broader aspects can be used for medicinal purposes and even adapted for rectal use. Between the container bottle and its elongated nozzle are located an intermediate bottle cap with a flat top having a ring of axial flow passages and a flexible valve disk positioned to overlie the flow passage outlets in said top. This combination functions as a check valve, permitting only one-way flow.

The nozzle is axially movable such that when in the retracted or closed position, an inner axially-facing circumferential shoulder in the base of the nozzle bears down on the periphery of the valve disk against the top of the cap causing the disk to block the outlets of the flow passages in said cap, thus preventing inflow or outflow of liquid or air from the container bottle through such outlets. Conversely, when the nozzle is in the extended or open position, the nozzle base no longer contacts the valve disk, so that when pressure is applied to the thin flexible walls of the container, liquid may flow out from the container through the outlets in the cap, past the flexed-open valve disk and out through the nozzle. However, when pressure is released, even though the nozzle is still in the open position, the resilient disk naturally flattens back against the cap outlets and thus acts as a check valve to prevent liquid and/or air backflow into the container.

In one of the broader aspects of the present invention, the cap and disk can be combined into a simplified unitary structure. In this case, the disk would normally lie flat in the closed position across the end of the bottle's neck in direct sealing contact with the top rim of the bottle's neck and be positioned in place by a depending stem which in turn is supported on a spider structure that snap locks into place within the neck of the bottle. The disk, stem, and spider would be molded as a single unit from plastic sufficiently flexible for the disk to function; and sufficiently stiff for the relatively thicker spider legs to hold the structure in place on the bottle's neck. When in the open position, the liquid content of the bottle would flow through the neck, past the legs of the spider structure, and out between the bottle neck's rim and flexed-open disk. When in the closed position, the outer rim of the disk would be held against the top rim of the bottle's neck by the aforementioned axial shoulder within the base of the nozzle.

Although this simplified structure is mechanically feasible, it presents several practical problems which serve to emphasize the even more surprising advantages of the preferred cap and disk embodiment of the present invention. To function, the unified structure would have to be made to very much closer and more costly tolerances. Molding would be more complex. Even though in the unitary structure only three pieces would be needed (the nozzle, the bottle and the unitary structure; as contrasted to four pieces in the cap-and-disk structure); and at least one assembly step probably would be saved (securing the disk onto the cap); nevertheless, the preferred cap-and-disk embodiment would overall be less expensive. The cost of the rubber used for the preferred disk would make the unitary structure prohibitively expensive, if molded entirely from the same material. Also, by making the cap and the disk separate, the material best suited for the intended use of each can be chosen (and not a compromise between conflicting needs of stiffness and flexibility, etc.). Finally, see the discussion below just before the description of the drawings, for a particular commercial advantage of the cap when contrastingly colored and positioned over the bottle's neck (versus the unitary structure mounted within the bottle's neck) due to the cap's visibility only when in the open position.

Numerous other advantages occur with the practice of any of the various embodiments of the present invention. For example, during shipment or storage with the nozzle positioned in the closed position, no liquid will flow out of the container. Thus this can be sold in a loose bag, or as a fail-safe, this could be alternatively handled and sold with a shrink band or other packaging which, until removed, prevents axial extension of the nozzle; thus securing the valve in the closed position. However, when the purchaser is ready to use the liquid content of the container, the nozzle may be readily positioned in the open position.

Controlled discharge of the bottle contents can advantageously be accomplished even with a single-handed manipulation. Should the initial discharge be incomplete, the one-way valve disk prevents back flow so that when further dispensing of liquid is required, further squeezing to exert further pressure on the body of the container will expel only additional contents from the container not previously dispensed. Thus, any concerned consumer is assured of receiving full value by use of all of the liquid content in the container.

The one-way valve feature of the instant invention also prevents the introduction of undesired substances, including air, back into the container while the nozzle is in the open position. This is both medically and esthetically important.

This container and nozzle assembly, for the same reason, will hold an initial prime, eliminating air from the nozzle, thereby greatly enhancing the ease of use, preventing injecting significant amounts of air into the vagina, and also eliminating waste of the container contents.

The function and structure of the intermediate cap could be incorporated into the neck of the container bottle. However, for various commercial and practical reasons this usually is not desirable. For example, it would be difficult to charge such a container through small flow passages equivalent to those located in the top of the cap. Alternatively, to charge such an already-formed container through a separate inlet, which would have to be subsequently sealed, would also be a difficult and costly operation.

Accordingly, the neck of the container bottle in the preferred embodiment has an external retention bead which snaps in behind a detent ring formed on the inner bore of the cap. The end of the bottle neck is dimensioned to be force-fit up into a longitudinally-extending circular groove having a chamfered inlet and being dimensioned to make a sealing interference fit with the end of the bottle neck. Thus, the cap is mechanically secured and fluid sealed onto the end of the bottle neck.

The cap has a flat end surface with a positioning stud centered to extend from the flat surface to position and hold the valve disk. A circular ring of axial flow holes surround the central stud extending from the outer top flat surface of the cap to the interior thereof thereby to form outlet passages from the container to the interior of the nozzle positioned over the cap.

The valve disk has a central hole (with a diameter preferably slightly smaller than the diameter of the stud on which it is mounted so as to prevent central leakage) and is shaped so that when secured on said stud it overlies the end face of the cap including the outlet passages.

The valve disk is retained on the central stud by spot melting the end of the stud ultrasonically or otherwise to overflow and retain the washer-shaped disk on the stud thus functioning as the plastic equivalent of a retaining rivet.

The outer cylindrical surface of the cap has a flat-bottomed circumferential recess with an upper sealing bead and a lower slope defining the axial extent of the recess.

The elongated nozzle has the usual internal passage with typical spray orifices at its tip and an enlarged hollow base extending the internal passage and dimensioned to fit snugly over the cap.

The internal bore of the nozzle base makes an interference fit with the sealing bead of the cap preventing leakage therepast. The nozzle base also has an internal circumferential retaining ring raised from the surface of its internal base, which ring is positioned to snap fit into and ride along the bottom of the external circumferential recess of the cap. This ring and the sealing bead axially overlap to prevent disassembly of the nozzle from the cap under normal use.

The inventive structure is uniquely constructed such that while the axial movement of the nozzle relative to the container between the open and closed positions is relatively easy, there is a positive resistance tending to lock the nozzle in either the closed or the open position; (1) to give adequate assurance of preventing leakage during storage when in the closed position and (2) to give effective positioning in the open position to prevent undesired closing during normal usage.

In the preferred embodiment, this is accomplished by a raised inclined detent ridge on the bottom outside surface of the cap interacting with a corresponding channel formed near the bottom of the bore of the nozzle base such that the bottom face of the channel mates with and bears on a sharply inclined bottom face of the detent when the nozzle is in the closed position, and the bottom most portion of the base is positioned slightly above the inclined detent ridge so as to be held by the detent in the open position even during use.

The container is typically at least a semi-transparent bottle so that the liquid content can be observed. The thin-wall container preferably is made by blow molding a low-density polyethylene. The nozzle preferably will also be made from a low-density polyethylene, but which is an opaque hygienically colored off-white or light beige and is formed by injection molding.

Preferably, the cap is made from a stiffer polypropylene plastic, also injection molded, in a contrasting color. The color difference has the advantage of being essentially hidden when the nozzle is in the closed position and yet being readily visible when in the open position to give a positive visual indication of the valve position of the assembly. The effectiveness of the sliding interference fits between the various parts is enhanced by having the cap made from a stiffer and different plastic relative to the other slide interfitting parts.

BRIEF DESCRIPTION OF THE DRAWINGS

In this specification and the accompanying drawings, applicant has shown and described several preferred embodiments of his invention and has suggested various alternatives and modifications thereto, but it is to be understood that these are not intended to be exhaustive and that many changes and modifications can be made within the scope of the invention. The suggestions herein are selected and included for purposes of illustration in order that others skilled in the art will more fully understand the invention and principles thereof and will thus be enabled to modify it and embody it in a variety of forms, each as may be best suited to the conditions of a particular use.

FIG. 1 is a perspective view of a preferred embodiment of the douche container and nozzle assembly showing the nozzle in the retracted, closed position. Broken lines indicate nozzle location in the extended, open position.

FIG. 2 is a longitudinal sectional view of the tip of the nozzle taken along lines 2—2 of FIG. 1.

FIG. 3 is a cross sectional view of the tip of the nozzle taken along lines 3—3 of FIG. 1.

FIG. 4 is a cross sectional view of the valve mechanism in the base of the nozzle taken along lines 4—4 of FIG. 1, showing the flexible valve disk mounted on the retaining stud and partially broken away to show flow passage outlets thereunder in the top face of the intermediate cap.

FIG. 5 is a longitudinal sectional view taken along lines 5—5 of FIG. 1, showing the container neck, intermediate cap, flexible valve disk and nozzle assembly in the closed position.

FIG. 6 is a longitudinal sectional view taken along lines 5—5 of FIG. 1 showing the container neck, intermediate cap, flexible disk and nozzle assembly in the open position, wherein the upwardly-directed flow-line arrows in the Figure indicate the direction of liquid outflow from the container through cap outlets, past the valve disk and on out through the nozzle.

FIG. 9 is a longitudinal sectional view (similar to FIG. 5), of an improved preferred embodiment of the present invention, showing an "extended stroke" structure with a flexible valve disk of longer diameter ratio relative to the nozzle passage, all with the nozzle assembly in the closed position.

FIG. 10 is a longitudinal sectional view (similar to FIG. 6) of the embodiment shown in FIG. 9, showing the same structure but in the open position.

DESCRIPTION OF PREFERRED EMBODIMENTS

Figure 7:
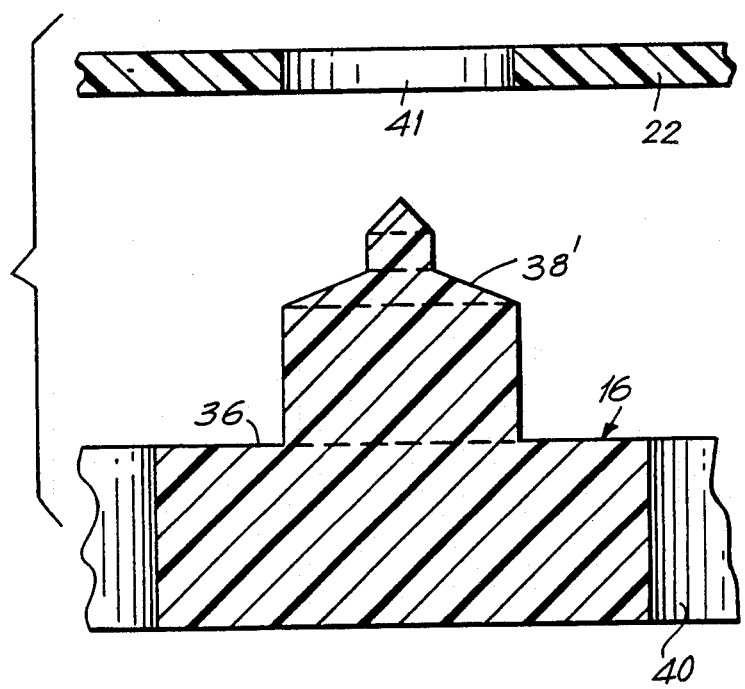
FIG. 7 is a pre-assembly cross sectional view of the valve disk and of the retaining stud therefor formed on the top face of the intermediate cap.

A better understanding of the preferred embodiment of the subject invention will follow from the subsequent written description considered in conjunction with the appended drawings.

Attention is initially directed to FIG. 1 of the drawings in which is illustrated a preferred embodiment of the invention, generally designated as assembly 10, including a container 12 and a nozzle 14. The nozzle 14 is illustrated in FIG. 1 in the retracted, or valve-closed position (see also FIG. 5), while broken lines indicate the nozzle 14 location when in the extended, or valve-open position (see also FIG. 6). The container 12 is stoppered by an intermediate cap 16 mounted to fit over the neck 18 of the container 12. As described below, certain features of the cap 16 and of the base 20 of the nozzle 14 co-act with a flexible valve disk 22 to constitute a valve mechanism which controls flow of fluids between the container 12 and its discharge nozzle 14.

The liquid solution 24 (as shown in FIG. 5) typically will be included when the product 10 is sold to the customer. The solution 24 is thus stored until used in the closed container 12. Advantageously, the container 12 is a flexible thin walled plastic bottle. The container volume may vary depending upon the desired amount of fluid content. The flexible thin wall permits the container to be easily collapsed by the user when the user squeezes the opened container to apply pressure to the fluid and expel the fluid from the container through the opened nozzle 14. This can advantageously be done with only one hand by pressing the side of the bottle inwardly with the fingers and palm of the hand.

The container 12 has a relatively thick walled open-ended neck 18. Near the base of the neck is a bulge in its wall known as a transfer bead 26, which aids in handling the weakwalled bottle during the assembly and filling process. This bulge 26 also gives a certain flexibility to the interfitted nozzle 14 and cap 16 relative to the container bottle 12 (which flexing is found to be desirable by some users).

The cap 16 and the neck 18 are shaped to snap together with a fluid-tight mechanical seal. The neck 18 has a detent ring 28 raised on the outer circumference of the neck 18, while the inner bore of the cap 16 near its open end has a corresponding raised detent ring 30. The base of the bore of cap 16 has an axially open circular groove 32 defined by the wall of the bore and a circular inner skirt 34. The groove 32 may be shaped to be slightly narrower than the wall of the open end of the neck 18; so that when the end of the neck 18 is seated in said groove 32, a sealing interference fit results.

In a preferred alternative, with the groove 32 being slightly wider than the thickness of the end wall of the neck 18, the inner circumference of the end of the neck 18 is sufficiently smaller than the outside diameter of the skirt 34, such that the skirt 34 makes a fluid-tight interference fit inside of the top of the neck 18.

The cap bore and the skirt 34 are slightly chamfered so as to flare the open end of the groove 32 to serve as a lead-in to aid in assembly. With the end of the neck 18 seated in the groove 32, the detent ring 30 within the cap 16 engages and bears against the inwardly-positioned axially-overlapping detent 28 of the neck 18 to lock the cap 16 in place over the end of the container neck 18.

The intermediate cap 16 has a flat top surface 36 and a raised retaining stud 38 centered thereon. A number of axial passages 40 extending from the interior of the cap through its top surface 36 ring the retaining stud 38.

The flexible valve disk or washer 22 is mounted on the retaining stud 38 and overlies the outlet of the axial passages 40. The number, shape, and placement of the passages 40 can be substantially varied, so long as the stud 38 is properly supported and the washer 22 effectively overlies the passage outlets.

Figure 8:
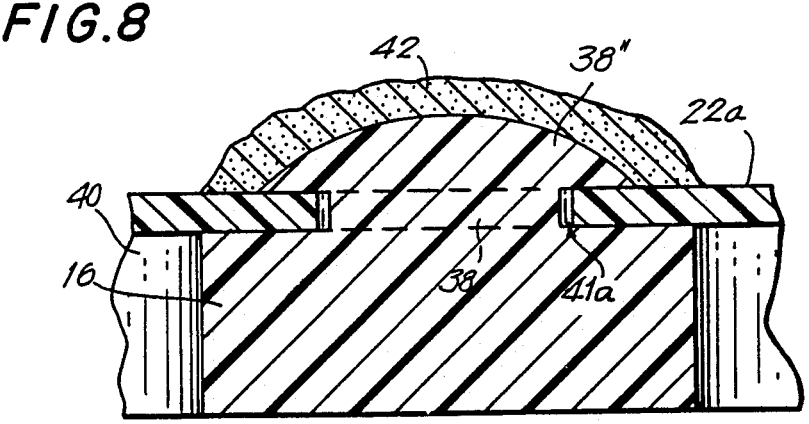
FIG. 8 is a cross sectional view of a modified embodiment of the valve disk with a relatively larger central hole assembled on a retaining stud with the end of the latter formed over into a mushroom shape to secure the disk and with silicone glue added as a sealant.

The valve disk 22 is made from an elastomer, preferably a silicone rubber. It is circular with a central hole 41. Preferably the central hole is slightly smaller than the diameter of the retaining stud 38, so as to seal effectively and prevent fluid escaping between the valve disk 22 and the stud 38. As shown in FIG. 7, the stud 38 can be shaped initially from a sloping narrowed end 38 to facilitate positioning the valve washer 22 on the stud 38. The end is then formed over, e.g. by heat, to make a retaining button 38" with a mushroom shape. Should leakage occur past the stud 38, silicone glue 42 can be applied over the button 38" as shown in FIG. 8. FIG. 8 also illustrates an alternative where the valve disk 22a has a central hole 41a with a diameter which is slightly larger than the diameter of the stud 38, to ease assembly; but would then require the use of the glue 42. Within the scope of this invention in its broader aspects, this structure could be reversed with the stud molded into the disk as an axial stem, and with a central hole in said cap 16 for receiving and holding said stem and thus positioning said disk. Also the stud 38 could be a separate piece that snaps into place through the hole 41 in the disk into a central hole in said cap 16.

As can be seen in FIG. 1, the nozzle 14 includes a hollow conventionally shaped upper body 44, which is elongated and slightly tapered, ending in a closed tip 46. The tip 46 has four longitudinal grooves 48 which are equally spaced around the circumference of the upper nozzle body 44. Each groove 48 contains two spray orifices 50 which communicate with the hollow center passageway 52 of the nozzle 14. Fluid from the container 12 is forced through the cap passages 40, past the valve disk 22, through the nozzle passageway 52 and out the spray orifices 50, to produce the desired douche action.

The intermediate cap 16 fits into the bore 54 of the nozzle base 20. The nozzle base 20 has an axially-facing shoulder 56 formed between the bore 54 of the nozzle base 20 and the passageway 52 of the upper nozzle body 44. The shoulder 56 is positioned to bear on the outer periphery of the valve disk 22, thus preventing flow of fluid from the container 12 through passages 40. The axial movement of the nozzle 14 relative to the intermediate cap 16 serves to position the shoulder 56 against, or spaced from, the valve disk 12, thereby respectively closing or opening the valve. These two positions are illustrated respectively in FIGS. 5 and 6. The arrows 58 in FIG. 6 show the flow path of the fluid out from the container 12 into the nozzle 14 past the flexed valve disk 22 when the nozzle 14 is in the extended open position, so the shoulder 56 is spaced away from the valve disk 22.

Referring to FIG. 5, it can be seen that the sealing bead 60 formed on the circumference of the cap 16 adjacent its top 36 makes a fluid tight interference fit with the bore 54 of the nozzle base 20. Below the bead 60 is a recess 62 in the outer circumferential surface of the cap 16, in which rides a retaining ring 64 that rises from about the middle of the bore 54 of the nozzle base 20. This ring 64 and bead 60 axially overlap thus preventing disassembly. They are also relatively positioned so as to limit the extent of axial movement of the nozzle into the extended position.

Such positioning means preferably is further provided with structure to secure the nozzle in the closed position with the shoulder 56 bearing in a positive manner against the valve disk as shown in FIG. 5, and also to hold the nozzle in the open position when in use as shown in FIG. 6. This is preferably accomplished by a raised doubly-inclined detent ridge 66 raised on the bottom outside circumferential surface of the cap 16 which interfits with a corresponding channel 68 at the bottom of the bore 54 of the nozzle base 20. The angle of the lower inclined face 70 of the channel 68 mates with and thus bears on a similarly inclined bottom face 72 of the detent 66 when the nozzle is in the closed position. The bottom-most portion 74 of the base 20 is dimensioned to be positioned slightly above the upper inclined surface of detent 66 (see FIG. 6) when the nozzle is in the open extended position, thereby resisting closing to the extent that the portion 74 engages the upper inclined face 76 of the detent ridge 66 in moving axially towards the closed position.

The positioning means could take other forms, such as having a circumferential groove at either end of the recess 62 into which the ring 64 can snap, to be retained respectively in the open or closed position (see a similar structure in the plug valve of the European patent 0177456).

This modification is more clearly illustrated in the improvement shown in FIGS. 9 and 10. For convenience, the structure in FIGS. 9 and 10 which is similar to that in FIGS. 5 and 6 are identified by the same reference numbers, but differentiated by the letter "a".

In the embodiment of FIGS. 9 and 10 relative to the embodiment of FIGS. 5 and 6 the nozzle 14a extends further axially when moved into the open position. This "extended stroke" raises the shoulder 56a further away from the cap's top surface 36a. This also permits use of a larger diameter disk 22a for a given bore of the nozzle passage 52a at the level of the shoulder 56a. As a result, the shoulder 56a can overlap the periphery of the disk 56a more and give a better seal, while still preventing the periphery of the disk 22a from hanging up on the shoulder 56a (which would tend to block flow of liquid therepast into the nozzle passage 52a). In other words, in the extended stroke structure shown in FIG. 10 with the radius of the disk 22a being substantially less than the distance from the center of the disk 22a to the closest portion of the shoulder 56a, the disk 22a cannot catch on the shoulder 56a.

Advantageously, the shoulder 56a at its inner corner has an axially depending lip 78. This serves to give a better sealing engagement between the shoulder 56a when pressed down on the outer periphery of the disk 22a against the surface 32a of the cap 16a. Preferably a raised circular bead 86 is formed in the top 36a of the cap 16a opposite said lip 78 to further aid in pinching of the flow of liquid past the sending disk 22a. As shown in the illustrated embodiment, the bead 86 has a slightly larger diameter than that of the lip 78, and is about one fourth the height.

In order to still permit flow even in the unlikely event that the disk 22a catches against the shoulder 56a (such as when only in a partially open position), the lip 78 of the shoulder 56a can have a castellated or a saw toothed form (not shown) allowing the liquid still to pass between the spaced teeth forming such a lip 78.

The cap 16a and the neck 18a of FIGS. 9 and 10, snap together in much the same way as the corresponding structure in FIGS. 5 and 6 as described above (with a detent "ring" 30a on the base of the cap 16a snapping behind the lower detent ring 28a on the lower outer portion of the neck 18a). Preferably the "ring" 30a can be symmetrically interrupted to form a series of circumferentially aligned engaging lugs 30a. Upper spacer ring 80 on the outer portion of the neck 18a forces the rim of the neck 18a against the skirt 34a of the cap 16a, thus assuring a fluid-tight seal between the cap 16a and the neck 18a.

The positioning means of the structure of FIGS. 9 and 10 differs somewhat from that of FIGS. 5 and 6. The nozzle base's retaining ring 64a still rides in the cap's outer recess 62a and interacts with the cap's upper sealing bead 60a to limit axial movement of the nozzle 14a in the extended position (as shown in FIG. 10). However, the latter are aided by an upper retention groove 82 (in the upper corner of the recess 62a which holds the nozzle 14a by means of the ring 64a being seated therein). Correspondingly a lower retention groove (in the lower corner of the recess 62a) serves to secure the nozzle 14a in the closed position as shown in FIG. 9, by means of the ring 64a seated the lower groove 84.

In yet another broader aspect of the invention, the cap 16 could be sealingly fastened onto the container neck 18 by a number of alternative ways including use of screw threads such as are used in conventional screw-on caps. This would be less preferred because of the comparatively easy and superior rapidity with which the illustrated nozzle and cap structure can be extracted from their respective molds; as contrasted to the more complex and slower removal of a screw structure from a screw shaped mold.

What is claimed is:

1. A douche container and nozzle assembly comprising
   a collapsible container which terminates in an open-ended neck;
   an intermediate cap mounted over the open end of said neck in a fluid-tight manner with at least one outlet passage through the top of said cap and in flow communication with said container, the top of said cap having a flat upper surface around any such opening, a circumferential sealing bead adjacent said top, and a retaining means;
   a flexible disk mounted on top of the cap by said retaining means, which disk sealing overlies each cap outlet passage;
   a nozzle with an internal passage extending from a distal tip to a proximal base having an enlarged bore in communication therewith which bore and passage together define a continuous substantially flat interior shoulder facing in the proximal axial direction, said cap closely fitting within said bore with its top facing the interior shoulder and with its sealing bead engaging the walls of the nozzle base bore to give a sliding fluid-tight seal;
   positioning means for retaining at least the top and sealing bead of said cap within the bore of said base and positively holding said cap either in a closed position with the cap top pressing the outer periphery of the disk against the interior shoulder so as to block flow of fluid through any cap outlet passages or in an open position under normal use conditions such that said disk is positioned axially spaced from said shoulder sufficiently to permit fluid flow communication past said disk from said neck to said internal passage while permitting manually overcoming said positive holding by axial displacement of said nozzle between said open and closed positions.

2. A douche container and nozzle assembly comprising
   (i) a collapsible container which terminates in an open-ended neck;
   (ii) a nozzle with an internal passage extending from a distal discharge tip to a proximal base having an enlarged bore in communication therewith, which enlarged bore and relatively narrower passage together define a continuous interior shoulder facing in the proximal axial direction;
   (iii) the container's open-ended neck and the nozzle's internal passage being in flow communication;
   (iv) a flexible disk positioned normally closed to overlie and obstruct the flow communication between the neck and the internal passage and capable of flexing open to permit such flow communication;
   (v) retaining means for securing said disk in position over the end of said neck;
   (vi) said neck fitting within said nozzle's base bore;
   (vii) sealing bead means positioned in the overlap between said neck and said base for making a sliding fluid-tight seal to prevent fluid escaping proximally from between said neck and said base, and
   (viii) positioning means for permitting restricted axial movement of said nozzle relative to said neck and for positively holding said nozzle moved either proximally into a closed position with its interior shoulder pressing on the outer periphery of the flexible disk so as to obstruct said flow communication or moved distally into an open position such that under normal use conditions said disk is positioned axially spaced from said shoulder sufficiently to permit fluid flow communication past said disk from within said neck to said internal passage while permitting manually overcoming said positive holding by axial displacement of said nozzle between said open and closed positions.

3. An apparatus according to claim 2, further comprising
   an intermediate cap having a top mounted over the open end of said neck in a fluid-tight manner with at least one outlet passage from within said neck through such top;

said retaining means positioned for mounting said flexible disk on top of the cap such that the disk sealingly overlies each cap outlet passage;

said cap closely fitting within the bore of said nozzle with its top facing and partially radially overlapping the nozzle's interior shoulder and with said sealing bead means formed on the outer periphery of said cap in the form of a circumferential sealing bead adjacent said top and engaging the walls of the nozzle base bore to give a sliding fluid-tight seal.

4. An apparatus according to claim 3, further comprising said cap being cup-shaped and having a flat top, said shoulder being generally correspondingly flat, and said disk being a normally-flat thin circular disk positioned to overlie the top of the cap and any outlet passage through said cap with the periphery of the disk radially overlapping the interior shoulder so as to be captured between the cap top and the shoulder when the nozzle is in the closed position.

5. An apparatus according to claim 4, further comprising said positioning means being a retaining ring formed on the interior of the bore of the nozzle base axially overlapping said sealing bead and spaced from said shoulder by an amount sufficient so as to engage said sealing bead and prevent disassembly when the nozzle is in the open position, and additionally by a recess in the circumference of said cap adjacent said bead on the side of the bead away from the shoulder, with said ring positioned to ride in said recess against said cap.

6. An apparatus according to claim 5, further comprising the recess of said positioning means in the outer circumference of said cap having dual grooves, one immediately above said recess and one immediately below said recess, into which said ring is positioned to be held in the respective open or closed position.

7. An apparatus according to claim 5, further comprising said positioning means additionally being a circumferential channel in the wall forming the bore of the nozzle base adjacent the open end of the bore opposite from said shoulder, a V-shaped detent ridge raised on the outer circumference of said cap at the end opposite said cap top, said detent ridge positioned to nest in said channel when in the closed position with said shoulder engaging said disk, a spacer bottom portion of said nozzle base extending between said open end and said channel which axially overlaps said detent ridge and in the open position engages the circumference of said cap on the side of the detent ridge which faces the cap top.

8. An apparatus according to claim 7, further comprising the channel being generally U-shaped in cross-section with the leg of the "U" facing the open end of the bore being inclined and positioned so as to bear on the similarly inclined face of said detent ridge opposite from said cap top.

9. An apparatus according to claim 6, further comprising the outer circumferential surface of the neck and the inner bore of the cap having raised detents which overlap and bear one on the other when said neck is seated within said cap.

10. An apparatus according to claim 9, further comprising said cap having an axially-depending interior skirt defining a circular interior groove into which the end of the container neck fits such that the end of said neck and said skirt form a fluid-tight interference fit.

11. An apparatus according to claim 10, further comprising said interior groove having a groove width between the exterior of said skirt and the interior of said cap which is slightly larger than the wall thickness of the end of the container neck, said skirt having an outside diameter slightly larger than the interior diameter of the said neck at the interior groove such that said neck when positioned in said interior groove makes an interference fit with said skirt.

12. An apparatus according to claim 11, further comprising a raised bead on one of the exterior of said neck or the interior of said cap so as to be positioned axially just below said skirt to enhance the interference fit at the skirt and thus the fluid-tight seal between the neck and the cap.

13. An apparatus according to claim 6, further comprising said retaining means being a stud positioned extending out from the center of the top of said cap, said disk being a circular rubber washer having a central hole which hole is slightly smaller than the diameter of the stud, and a fastening means for holding said washer against the flat top of said cap by its center.

14. An apparatus according to claim 13, further comprising the top of the stud being formed over into a retaining button.

15. An apparatus according to claim 13, further comprising a plurality of outlet passages ringing said stud.

16. An apparatus according to claim 10, further comprising said neck, said cap, and said nozzle base bore being generally of a circular cylindrical shape and said shoulder and said disk being circular.

17. An apparatus according to claim 16, further comprising said outlet passages being eight circular holes aligned in a circular ring centered on the axis of said cap.

18. An apparatus according to claim 10, further comprising the shoulder being substantially flat and with a small circular lip having a radius smaller than that of the disk and extending in the proximal axial direction from adjacent the nozzle passage.

19. An apparatus according to claim 18, further comprising a small circular raised bead on the top of the cap and having a radius approximately the same as said lip.

20. A douche container and nozzle assembly comprising a collapsible container which terminates in a neck;

a cup-shaped intermediate cap mounted on the neck, which cap has a flat top, a circumferential sealing bead adjacent said top, at least one outlet passage through said top and in flow communication with said container, and a retaining means;

a normally-flat flexible disk mounted on top of the cap by said retaining means, which disk overlies each cap outlet passage;

a nozzle with an internal passage having a base with an enlarged bore in communication therewith which together define a continuous axially-facing flat interior shoulder, said cap closely fitting within said bore with its top facing the interior shoulder and with its sealing bead engaging the walls of the nozzle base bore to give a sliding fluid-tight seal;

positioning means for retaining at least the top and sealing bead of said cap within the bore of said base and positively holding said cap either in a closed position with the cap top pressing the outer periphery of the disk against the interior shoulder so as to block flow of fluid through any cap outlet passages or in an open position under normal use conditions with said cap held with its top positioned axially spaced from said shoulder sufficiently to permit fluid flow through at least one cap outlet passage and out past said disk while permitting manually overcoming said positive holding by axial displacement of said nozzle relative to said cap between said open and closed positions.

21. An apparatus according to claim 20, wherein said retaining means is a stud positioned extending out from the center of the top of said cap, said disk is a circular rubber washer having a central hole which hole is slightly smaller than the diameter of the stud, and the top of the stud is formed over into a retaining button to hold said washer against the flat top of said cap by its center.

22. An apparatus according to claim 21, wherein said positioning means comprises a retaining ring formed on the interior of the bore of the nozzle base axially overlapping said sealing ring and spaced from said shoulder by an amount sufficient so as to engage said sealing bead and prevent disassembly when the nozzle is in the open position and further comprising a recess in the circumference of said cap adjacent said bead on the side of the bead away from the shoulder, with said ring positioned to ride in said recess against said cap.

23. An apparatus according to claim 22, wherein the outer circumferential surface of the neck and the inner bore of the cap have raised detents which overlap and bear one on the other so as to fix said neck within said cap.

24. An apparatus according to claim 23, wherein there are a plurality of outlet passages ringing said stud.

25. An apparatus according to claim 24, wherein said neck, said cap, and said nozzle base bore are generally of a circular cylindrical shape and said shoulder and said disk are circular.

26. An apparatus according to claim 25, wherein said cap has an axially-depending interior skirt defining a circular groove into which the end of the container neck fits such that the end of said neck and said skirt form a fluid-tight interference fit.

27. An apparatus according to claim 26, wherein said outlet passages are eight circular holes aligned in a circular ring centered on said stud.

28. An apparatus according to claim 26, wherein said positioning means further comprises a circumferential channel in the wall forming the bore of the nozzle base adjacent the open end of the bore opposite from said shoulder, a V-shaped detent ridge raised on the outer circumference of said cap at the end opposite said cap top, said detent ridge positioned to nest in said channel when in the closed position with said shoulder engaging said disk, a spacer bottom portion of said nozzle base extending between said open end and said channel which axially overlaps said detent ridge and in the open position engages the circumference of said cap on the side of the detent ridge which faces the cap top.

29. An apparatus according to claim 28, wherein the channel is generally U-shaped in cross-section with the leg of the "U" facing the open end of the bore being inclined and positioned so as to bear on the similarly inclined face of said detent ridge opposite from said cap top.

30. An apparatus according to claim 25, wherein said cap has an axially-depending interior skirt defining a circular groove having a groove width slightly smaller than the end of the container neck such that said neck is positioned therein with an interference fit.

31. An apparatus according to claim 25, wherein said cap has an axially-depending interior skirt defining a circular groove having a groove width between the exterior of said skirt and the interior of said cap which is slightly larger than the wall thickness of the end of the container neck, said skirt having an outside diameter slightly larger than the interior diameter of the said neck at the groove such that said neck when positioned in said groove makes an interference fit with said skirt.

* * * * *